(12) United States Patent
Didier et al.

(10) Patent No.: US 7,491,747 B2
(45) Date of Patent: Feb. 17, 2009

(54) BUTYRIC ACID DERIVATIVES

(75) Inventors: Roche Didier, Lyons (FR); Jean-Jacques Zeiller, Lyons (FR); Francis Contard, Lyons (FR); Valérie Guyard-Dangremont, Saint Maurice de Gourdans (FR); Daniel Guerrier, Saint Genis Laval (FR); Hervé Dupont, Lyons (FR); Jean-Jacques Berthelon, Lyons (FR)

(73) Assignee: Merck Patent GmbH, Darmstadt (DE)

( * ) Notice: Subject to any disclaimer, the term of this patent is extended or adjusted under 35 U.S.C. 154(b) by 365 days.

(21) Appl. No.: 10/485,205

(22) PCT Filed: Jul. 3, 2002

(86) PCT No.: PCT/EP02/07383

§ 371 (c)(1), (2), (4) Date: Sep. 15, 2004

(87) PCT Pub. No.: WO03/011819

PCT Pub. Date: Feb. 13, 2003

(65) Prior Publication Data

US 2005/0020651 A1    Jan. 27, 2005

(30) Foreign Application Priority Data

Jul. 30, 2001 (FR) .................. 01 10198

(51) Int. Cl.
*A61K 31/19* (2006.01)
*C07C 321/00* (2006.01)
*C12P 7/52* (2006.01)

(52) U.S. Cl. .................. 514/557; 560/9; 435/141

(58) Field of Classification Search ................. 514/557; 560/9; 435/141
See application file for complete search history.

(56) References Cited

U.S. PATENT DOCUMENTS

| 6,013,649 A * | 1/2000 | Freskos et al. ............ 514/237.8 |
| 6,100,266 A | 8/2000 | Baxter et al. |
| 2001/0008947 A1 | 7/2001 | Varasi et al. |
| 2002/0103239 A1 | 8/2002 | Bedell et al. |

FOREIGN PATENT DOCUMENTS

| DE | 2161991 | 6/1973 |
| HU | P9501146 | 10/1995 |
| HU | P9902437 | 12/1999 |
| JP | 02-193942 | * 7/1990 |
| WO | WO 9803164 | 1/1998 |
| WO | WO 9839316 | 9/1998 |

OTHER PUBLICATIONS

Expert Opinion, vol. 11(3), pp. 379-401, 2006.*
Patent Abstracts of Japan vol. 1997, No. 09, Sep. 30, 1997 & JP 09136873 A (Fuji Chemical Industry), May 27, 1997 abstract.
Patent Abstracts of Japan vol. 2000, No. 14, Mar. 5, 2001 & JP 2000309573 A (Fuji Chemical Industry), Nov. 7, 2000 abstract.
M. Terada, et al.: "Enantiomerically pure compound synthesis by asymmetric glyoxylate-ene reaction with vinylic sulphides and selenides catalysed by a chiral titanium complex" Journal of the Chemical Society, Chemial Communications, No. 3, Feb. 7, 1993, pp. 327-328, XP002195871.
D. C. Lathbury, et al.: " A route to the pyrrolizidone ring system using a novel radical cyclisation" Journal of the Chemical Society, Chemial Communications, No. 2, Jan. 15, 1988, pp. 81-82, XP002195872.
T. Konno, et al.: "Synthesis and application of a alpha-trifluoromethylated aldehydes" Tetrahedron, vol. 52, No. 1, Jan. 1, 1996 pp. 199-208, XP004104597.
P. Renaud , et al.: "Use of O, Se-acetals for radical-mediated phenylseleno group transfer reactions" Synthesis, No. 2, Feb. 1996, pp. 253-258, XP002195873.
Y. Gao, et al.: "Stereoselective synthesis of meso-2,6-diaminopimelic acid and its selectively protected derivatives" Journal of Organic Chemsitry, vol. 63, No. 7,Apr. 3, 1998 pp. 2133-2143 XP002195874.
L.J. Jolivette, et al.: "Thietanium ion formation from the food mutagen 2-chloro-4-(methylthio)butanoic acid" Chemical Research in Toxicology, vol. 11, No. 7, May 30, 1998 pp. 794-799, XP002195875.
A.K. Ghosh, et al.: "Synthetic studies of antitumour macrolide laulimalide: a stereoselective synthesis of the C17-C28 segment" Tetrahedron Letters, vol. 41, No. 24, Jun. 2000 pp. 4705-4708 XP004205603.
E. Yoshii, et al.: "Introduction of a 3-alkoxycarbonyl-2-propenyl group at the ortho position of phenol and naphthol via alpha-aryloxy-gamma-butyrolactone. Application to synthesis of (+−)-nanaomycin A and a 1-anthracenone" Chemical and Pharmaceutical Bulletin, vol. 32, No. 12, Dec. 1984 pp. 4779-4785, XP002195877.
J.-G. Boiteau, et al.: "A new, ring closing metathesis-based synthesis of (−)-fumagillol" Organic Letters, vol. 3, No. 17, Jul. 31, 2001 pp. 2737-2740, XP002195876.

* cited by examiner

*Primary Examiner*—Rei-tsang Shiao
*Assistant Examiner*—Susannah Chung
(74) *Attorney, Agent, or Firm*—Millen, White, Zelano, Branigan, P.C.

(57) ABSTRACT

The present invention relates to a compound of the formula I: (Formula I) in which: A, B, $R^1$, Z, n and $R^2$ are as defined in claim 1. These compounds are useful in the treatment of dyslipidaemia, atherosclerosis and diabetes.

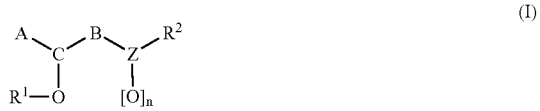

(I)

14 Claims, No Drawings

BUTYRIC ACID DERIVATIVES

The present invention relates to 4-(arylthio)- or (4-heteroarylthio)butyric acid derivatives that may be used in the treatment of dyslipidaemia, atherosclerosis and diabetes, to pharmaceutical compositions comprising them and to processes for preparing these compounds.

The invention also relates to the use of these compounds for the production of medicaments intended for treating dyslipidaemia, atherosclerosis and diabetes.

In most countries, cardiovascular disease remains one of the major diseases and the main cause of death. About one third of men develop a major cardiovascular disease before the age of 60, with women showing a lower risk (ratio of 1 to 10). With advancing years (after the age of 65, women become just as vulnerable to cardiovascular diseases as men), this disease increases even more in scale. Vascular diseases, such as coronary disease, strokes, restenosis and peripheral vascular disease, remain the prime cause of death and handicap throughout the world.

Whereas diet and lifestyle can accelerate the development of cardiovascular diseases, a genetic predisposition leading to dyslipidaemia is a significant factor in cardiovascular accidents and death.

The development of atherosclerosis appears to be linked mainly to dyslipidaemia, which means abnormal levels of lipoproteins in the blood plasma. This dysfunction is particularly evident in coronary disease, diabetes and obesity.

The concept intended to explain the development of atherosclerosis was mainly focused on the metabolism of cholesterol and on the metabolism of triglycerides.

However, since the studies of Randle et al. (Lancet, 1963, 785-789), a novel concept has been proposed: a glucose-fatty acid cycle or Randle cycle, which describes the regulation of the equilibrium between the metabolism of lipids in terms of triglycerides and cholesterol, and the oxygenation of glucose. According to this concept, the inventors have developed a novel programme, the aim of which is to find novel compounds acting simultaneously on lipid metabolism and glucose metabolism.

Fibrates are well-known therapeutic agents with a mechanism of action via the "Peroxisome Proliferator Activated Receptors". These receptors are the main regulators of lipid metabolism in the liver (PPARα isoform). In the last 10 years, thiazolidinediones have been described as powerful hypoglycaemiant agents in man and animals. It has been reported that thiazolidinediones are powerful selective activators of another isoform of PPARs: PPARγ (Lehmann et al., J. Biol. Chem., 1995, 270, 12953-12956).

The inventors have discovered a novel class of compounds that are powerful activators of the PPARα and PPARγ isoforms. On account of this activity, these compounds have a considerable hypolipidaemiant and hypoglycaemiant effect.

The compounds of the invention correspond to formula (I) below:

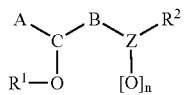

I in which:

A represents carboxyl; $(C_6$-$C_{18})$aryloxycarbonyl in which the aryl group is optionally substituted; $(C_1$-$C_{14})$alkoxycarbonyl in which the alkyl group is optionally substituted; —CO—NHOH; -tetrazolyl;

B represents an optionally substituted ethylene group —CH$_2$—CH$_2$—;

R$^1$ represents a hydrogen atom; optionally substituted $(C_1$-$C_{14})$alkyl; optionally substituted $(C_6$-$C_{18})$aryl; optionally substituted heteroaryl; $(C_6$-$C_{18})$aryl$(C_1$-$C_{14})$alkyl in which each of the aryl and/or alkyl radicals are optionally substituted; and heteroaryl$(C_1$-$C_{14})$alkyl in which each of the heteroaryl and/or alkyl radicals are optionally substituted;

Z represents S or Se;

n is an integer equal to 0, 1 or 2;

R$^2$ represents optionally substituted $(C_6$-$C_{18})$aryl; optionally substituted heteroaryl; or optionally substituted heterocycle containing an aromatic moiety; and when R$^1$ represents optionally substituted $(C_6$-$C_{18})$aryl, then R$^2$ can also represent $(C_1$-$C_{14})$alkyl;

it being understood that when R$^1$ represents naphthyl or 4-methoxyphenyl, A represents carboxyl or methoxycarbonyl, B represents ethylene, n represents 0, and Z represents S or Se, then R$^2$ does not represent phenyl, the stereoisomers thereof and the addition salts thereof with acids or bases.

In the context of the invention, the term "alkyl" means a linear or branched hydrocarbon-based chain containing from 1 to 14 carbon atoms, preferably from 1 to 10 and better still from 1 to 6 carbon atoms, for example from 1 to 4 carbon atoms.

Examples of alkyl radicals are methyl, ethyl, propyl, isopropyl, butyl, iso-butyl, t-butyl, pentyl, isopentyl, neopentyl, 2-methylbutyl, 1-ethylpropyl, hexyl, isohexyl, neohexyl, 1-methylpentyl, 3-methylpentyl, 1,1-dimethylbutyl, 1,3-dimethylbutyl, 2-ethylbutyl, 1-methyl-1-ethylpropyl, heptyl, 1-methylhexyl, 1-propylbutyl, 4,4-dimethylpentyl, octyl, 1-methylheptyl, 2-methylhexyl, 5,5-dimethylhexyl, nonyl, decyl, 1-methylnonyl, 3,7-dimethyloctyl and 7,7-dimethyloctyl-octyl radicals.

The term "aryl group" means a monocyclic or polycyclic carbocyclic aromatic group containing from 6 to 18 carbon atoms.

Aryl groups that may be mentioned include phenyl, naphthyl, anthryl and phenanthryl.

The heteroaryl groups are monocyclic or polycyclic heterocyclic aromatic groups comprising hetero atoms generally chosen from O, S and N, optionally in oxidised form (in the case of S and N).

Preferably, at least one of the monocydes constituting the heterocycle comprises from 1 to 4 endocyclic hetero atoms and better still from 1 to 3 hetero atoms.

Preferably, the heterocycle consists of one or more monocycles each being 5- to 7-membered.

Examples of 5- to 7-membered monocyclic heteroaryls are especially pyridine, furan, thiophene, pyrrole, pyrazole, imidazole, thiazole, isoxazole, isothiazole, furazane, pyridazine, pyrimidine, pyrazine, thiazines, oxazole, pyrazole, oxadiazole, triazole and thiadiazole.

Examples of bicyclic heteroaryls in which each monocycle is 5- to 7-membered are chosen from indolizine, indole, isoindole, benzofuran, benzothiophene, indazole, benzimidazole, benzothiazole, benzofurazane, benzothiofurazane, purine, quinoline, isoquinoline, cinnoline, phthalazine, quinazoline, quinoxaline, naphthyridines, pyrazolotriazine (such as pyrazolo-1,3,4-triazine), pyrazolepyrimidine and pteridine.

Preferred heteroaryls that may be mentioned include quinolyl, pyridyl, benzothiazolyl and triazolyl.

The tricyclic heteroaryls in which each monocycle is 5- to 7-membered are chosen, for example, from acridine, phenazine and carbazole.

According to the invention, the expression "heterocycle containing an aromatic moiety" means a heterocycle consisting of one or more monocydes each preferably being 5- to 7-membered, in which at least one of the monocycles is aromatic, and at least one of the monocydes is heterocyclic and in which the monocycles are ortho- or peri-fused in pairs. It should be understood that the non-aromatic monocycles may be saturated or unsaturated and that the aromatic monocycle is heterocyclic or non-heterocyclic. The heterocyclic monocycle(s) contain(s) one or more endocyclic hetero atoms (preferably 1 to 4 and better still 1 to 3) chosen from O, N and S, optionally in oxidised form (in the case of S or N).

The carbocyclic aromatic monocydes of the heterocycle containing an aromatic moiety are preferably phenyl nuclei.

The heterocyclic aromatic monocycles of the heterocycle containing an aryl moiety are preferably pyridine, furan, thiophene, pyrrole, pyrazole, imidazole, thiazole, isoxazole, isothiazole, furazane, pyridazine, pyrimidine, pyrazine, thiazine, oxazole, oxadiazole, triazole or thiadiazole nuclei.

The heterocyclic saturated monocydes of the heterocycle containing an aryl moiety are, for example, tetrahydrofuran, dioxolane, imidazolidine, pyrazolidine, piperidine, dioxane, morpholine, dithiane, thiomorpholine, piperazine, trithiane, oxepine or azepine nuclei. The heterocycle containing an aryl moiety can contain one or more unsaturated monocydes derived from the aromatic or heterocyclic monocydes described above.

The heterocycle containing an aryl moiety is monocyclic or polycyclic, preferably bicyclic or tricyclic.

It should be understood that each of the saturated and/or unsaturated monocydes in the heterocycle containing an aryl moiety can be substituted by oxo.

Examples of heterocycles containing an aryl moiety are especially the nuclei of the formulae:

B1:

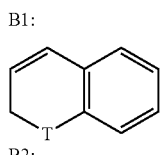

B2:

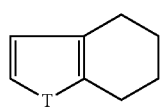

B3:

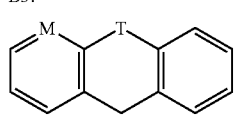

B4:

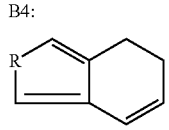

B5:

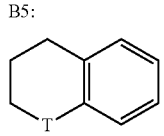

B6:

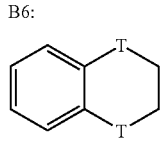

B7:

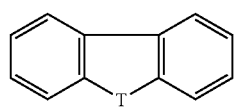

B8:

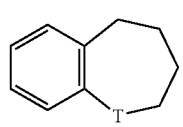

B9:

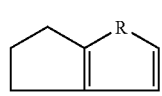

B10:

B11:

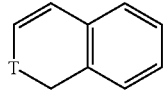

B12:

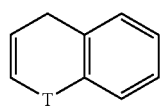

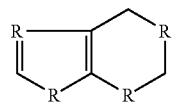

in which M and T are independently chosen from O, S, SO$_2$, N and C, it being understood that each of the nuclei B1 to B12 includes at least one hetero atom optionally in oxidised form, and R is chosen from O, S and N.

According to the preferred embodiments of the invention:

T represents O, S or SO$_2$ and M represents N or C. Preferably, in B1, T represents O; in B2, T represents O or S; in B3, T represents SO$_2$ or O and M represents C or N; in B4, R represents S; in B5, T represents O; in B6, T represents O; in B7, T represents O; in B8, T represents O; in B9, R represents S; in B10, T represents O; in B11, T represents O; in B12, R represents N.

When M, T or R represents N, this nitrogen is preferably substituted by a hydrogen atom, with alkyl or with alkylcarbonyl.

Preferably, the heterocycle containing an aryl moiety has the formula:

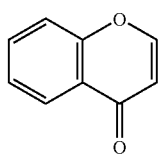

The substituents on the aryl groups, heteroaryl groups containing an aromatic moiety and heteroaryl groups are chosen from halogen atoms; cyano; nitro; optionally halogenated ($C_1$-$C_{14}$)alkoxy (and preferably trifluoromethoxy); optionally halogenated ($C_1$-$C_{14}$)thioalkoxy, preferably ($C_1$-$C_{10}$)thioalkoxy; optionally halogenated and preferably perhalogenated ($C_1$-$C_{14}$)alkyl (especially methyl or trifluoromethyl); ($C_1$-$C_{14}$)alkylcarbonyl in which the alkyl moiety is optionally halogenated; ($C_6$-$C_{18}$)arylcarbonyl in which the aryl moiety is optionally substituted one or more times by halogen, optionally halogenated ($C_1$-$C_{14}$)alkyl and optionally halogenated ($C_1$-$C_{14}$)alkoxy; ($C_1$-$C_{14}$)alkylcarbonylamino in which the alkyl moiety is optionally halogenated; ($C_6$-$C_{18}$)arylcarbonylamino in which the aryl moiety is optionally substituted one or more times by halogen, optionally halogenated ($C_1$-$C_{14}$)alkyl and optionally halogenated ($C_1$-$C_{14}$)alkoxy; and ($C_6$-$C_{18}$)aryl optionally substituted one or more times by halogen, optionally halogenated ($C_1$-$C_{14}$)alkyl such as trifluoromethyl, and optionally halogenated ($C_1$-$C_4$)alkoxy such as trifluoromethoxy.

The term "halogen" especially means a chlorine, bromine, iodine or fluorine atom.

The acyl groups, heteroaryl groups and heterocyclic groups containing an aromatic moiety can be substituted one or more times by the substituents listed above, preferably one to three times, for example one or two times.

The alkyl group of the alkoxycarbonyl, alkyl, arylalkyl and heteroarylalkyl radicals and also the ethylene group representing B may be substituted by one or more radicals independently chosen from halogen, ($C_1$-$C_{14}$)alkoxy, ($C_1$-$C_{14}$)thioalkoxy, cyano and nitro, preferably with one to three radicals of this type.

In a particularly preferred manner, $R^1$ represents benzyl optionally substituted on the phenyl nucleus; optionally substituted phenyl; or optionally substituted pyridyl; the substituents on the phenyl nuclei and on the pyridyl nucleus preferably being chosen from halogen atoms and cyano, trifluoromethyl, ($C_1$-$C_6$)alkyl or ($C_1$-$C_6$)alkoxy groups or a ($C_6$-$C_{18}$)aryl group (such as phenyl), itself optionally substituted by halogen, ($C_1$-$C_6$)alkyl, ($C_1$-$C_6$)alkoxy, $CF_3$ or CN.

Advantageously, $R^2$ represents optionally substituted phenyl; optionally substituted benzopyridine; optionally substituted benzothiazole; optionally substituted naphthyl; optionally substituted quinolyl; optionally substituted triazole; or the radical:

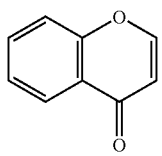

which is optionally substituted.

Preferred substituents of these radicals representing $R^2$ are halogen atoms or CN, $CF_3$, ($C_1$-$C_6$)alkyl, ($C_1$-$C_6$)alkoxy or ($C_6$-$C_{18}$)aryl groups such as phenyl, itself optionally substituted by halogen, ($C_1$-$C_6$)alkyl, ($C_1$-$C_6$)alkoxy, $CF_3$ or CN.

A preferred meaning of A that may be mentioned is —COOH.

Compounds that are particularly preferred in the invention are those for which B represents ethylene.

Another group of preferred compounds consists of compounds in which Z represents S and n represents 0, 1 or 2.

The following compounds are most particularly preferred:

2-(dibenzofuran-2-yloxy)-4-m-tolylsulphanylbutyric acid 2-(dibenzofuran-2-yloxy)-4-(2,4-dimethylphenylsulphanyl)butyric acid 4-m-tolylsulphanyl-2-(4-trifluoromethoxyphenoxy)butyric acid 2-(4-chlorophenoxy)-4-(2,4-dimethylphenylsulphanyl)butyric acid 2-(3,4-dichlorophenoxy)-4-(2,5-dimethylphenylsulphanyl)butyric acid 4-(2,4-dimethylphenylsulphanyl)-2-(4-methoxyphenoxy)butyric acid 4-(2,4-dimethylphenylsulphanyl)-2-(4-fluorophenoxy)butyric acid 4-(2,4-dimethylphenylsulphanyl)-2-(3-trifluoromethylphenoxy)butyric acid 4-(2,5-dimethylphenylsulphanyl)-2-(4-methoxyphenoxy)butyric acid 2-(4-cyanophenoxy)-4-(2,5-dimethylphenylsulphanyl)butyric acid 2-(4-chloro-2-methoxyphenoxy)-4-(2,5-dimethylphenylsulphanyl)butyric acid 2-(4-chloro-3-ethylphenoxy)-4-(2,5-dimethylphenylsulphanyl)butyric acid 2-(4-chloro-2-methoxyphenoxy)-4-(naphthalen-1-ylsulphanyl)butyric acid 2-(4-chlorophenoxy)-4-(2-ethylphenylsulphanyl)butyric acid 4-(2-ethylphenylsulphanyl)-2-(4-methoxyphenoxy)butyric acid 2-(4-fluorophenoxy)-4-o-tolylsulphanylbutyric acid 4-(2,4-dimethylphenylsulphanyl)-2-(4-trifluoromethylphenoxy)butyric acid 4-(2,5-dimethylphenylsulphanyl)-2-(4-trifluoromethylphenoxy)butyric acid 4-m-tolylsulphanyl-2-(4-trifluoromethylphenoxy)butyric acid 4-(3-chlorophenylsulphanyl)-2-(4-trifluoromethylphenoxy)butyric acid 4-o-tolylsulphanyl-2-(4-trifluoromethylphenoxy)butyric acid (R)-4-o-tolylsulphanyl-2-(4-trifluoromethylphenoxy)butyric acid (S)-4-o-tolylsulphanyl-2-(4-trifluoromethylphenoxy)butyric acid 4-phenylsulphanyl-2-(4-trifluoromethylphenoxy)butyric acid.

It should be understood that the compounds of the formulae:

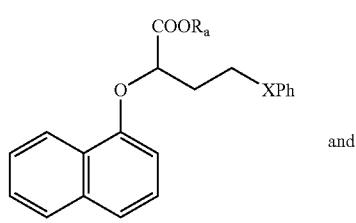

and

-continued

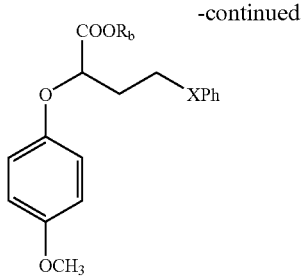

in which
X represents S or Se; and
$R_a$ is chosen from a halogen atom and a methyl group; and
$R_b$ represents methyl, are excluded from the subject of the present invention since they have already been described, as intermediate compounds, in Chem. Pharm. Bull. 32 (12) 4779-4785 (1984) and/or J. Org. Chem. 1983, 48, 2630-2632.

When the compound of the formula I comprises an acid function, and for example a carboxylic function, this compound can form a salt with a mineral or organic base.

As examples of salts with organic or mineral bases, mention may be made of the salts formed with metals, and especially alkali metals, alkaline-earth metals and transition metals (such as sodium, potassium, calcium, magnesium or aluminium), or with bases such as ammonia or secondary or tertiary amines (such as diethylamine, triethylamine, piperidine, piperazine or morpholine) or with basic amino acids, or with osamines (such as meglumine) or with amino alcohols (such as 3-aminobutanol and 2-aminoethanol).

When the compound of the formula I comprises a basic function, and for example a nitrogen atom, this compound can form a salt with an organic or mineral acid.

The salts with organic or mineral acids are, for example, the hydrochloride, hydrobromide, sulphate, hydrogen sulphate, dihydrogen phosphate, citrate, maleate, fumarate, 2-naphthalenesulphonate and para-toluenesulphonate.

The invention also covers salts that allow a suitable separation or crystallisation of the compounds of the formula I, such as the salts obtained with chiral amines.

The invention also covers the stereoisomers of the compounds of the formula I, and also mixtures of stereoisomers in all proportions.

The compounds of the formula I may be readily prepared by carrying out any one of the following processes.

A) Preparation of the compounds of the formula I in which A represents COOH and Z represents S with n=0.

The compounds of the formula I in which A=COOH; Z=S and n=0 may especially be obtained by reacting a compound of the formula II:

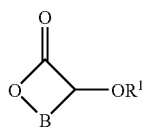

II in which B and $R^1$ are as defined in claim 1, with a thiol of the formula III:

$$R^2\text{---SH} \qquad \text{III}$$

in which $R^2$ is as defined above for formula I, in the presence of a base.

The bases that may be used are organic or mineral bases such as, for example, a hydroxide (such as an ammonium or alkali metal hydroxide), a carbonate (such as an alkali metal or alkaline-earth metal carbonate), an alkali metal alkoxide, an organic hydride (such as alkali metal hydrides), an alkali metal amide, an alkali metal fluoride, ammonium fluoride, ammonia, triethylamine, tributylamine, pyridine or N-methylmorpholine.

Preferred bases that will be mentioned include sodium carbonate, sodium hydride, caesium carbonate, potassium carbonate, sodium tert-butoxide and potassium tert-butoxide.

The reaction is preferably carried out in a polar aprotic solvent, such as a nitrile (for example acetonitrile or isobutyronitrile), an amide (such as formamide, dimethylformamide, N-methyl-2-pyrrolidinone or hexylmethylphosphorylamide, a halogenated hydrocarbon (such as methylene fluoride, chloroform, carbon tetrachloride, dichloroethane, chlorobenzene or dichlorobenzene), or a mixture of these solvents in any proportions. Advantageously, the reaction is performed in dimethylformamide.

The reaction temperature will be set by a person skilled in the art as a function of the base used, the solvent chosen and the reactivity of the compounds present.

When the solvent used is dimethylformamide and the base is an alkali metal carbonate or a hydride such as an alkali metal hydride, or an alkali metal fluoride, the temperature is advantageously maintained between 80 and 150° C. and better still between 90 and 130° C.

A reaction time of 30 minutes to 5 hours and preferably of 1 hour to 3 hours is usually sufficient.

B) Preparation of the Compounds of the Formula I in which A Represents —COOH and Z Represents Se with n=0

The compounds of the formula I in which A=COOH, Z=Se and n=0 may be prepared by reacting a selenium compound of the formula IV:

$$R^2\text{---Se---Se---}R^2 \qquad \text{IV}$$

in which $R^2$ is as defined above for formula I with a hydride such as a borohydride or aluminohydride, followed by reaction of the resulting compound with a compound of the formula II:

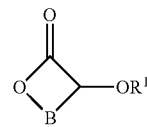

II in which B and $R^1$ are as defined above for formula I.

In the first step, the bases that may be used are especially those as defined above. Preferred hydrides that will be used are alkali metal borohydrides such as sodium borohydride.

Solvents that may especially be used include any polar aprotic solvent recommended above for the reaction of the lactone of the formula II with the thiol of the formula III. Dimethylformamide is a solvent that is particularly preferred for this step.

A person skilled in the art will advantageously set the temperature for this step between 80 and 150° C. and preferably between 90 and 130° C., as a function of the base and the solvent selected.

Usually, the reaction time is between 30 minutes and 6 hours, for example between 1 hour and 3 hours.

The second step, which comprises the reaction of the lactone of the formula II with the compound obtained in the preceding step, is advantageously performed in a polar aprotic solvent preferably chosen from a halogenated hydrocarbon, an amide or a nitrile such as those defined above. More particularly, this reaction will be performed in dimethylformamide.

In this case also, a reaction temperature of between 80 and 150° C. is particularly suitable. Similarly, a reaction time of between 30 minutes and 5 hours allows the isolation of sufficient amounts of the expected product of the formula I.

C) Preparation of the Compounds of the Formula I in which Z Represents Se or S and n is Other than 0.

The compounds of the formula I in which n is non-zero may be obtained by reacting an oxidising agent with the corresponding compound of the formula I in which n=0:

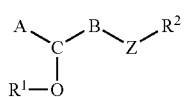

Ia in which A, $R^1$, $R^2$ and B are as defined above for formula I and Z represents S or Se, with a suitable oxidising agent.

Among the oxidising agents that may be used, meta-chloroperbenzoic acid, the acetic acid/$CrO_3$ mixture, magnesium dioxide, sodium dichromate combined with sulphuric acid, selenium dioxide, sodium hypobromite or silver oxide may especially be selected. A preferred oxidising agent that will be used is m-chloroperbenzoic acid (m-CPBA).

The oxidation reaction is preferably performed in a solvent chosen from a halogenated hydrocarbon (such as methylene chloride, chloroform, carbon tetrachloride, dichloroethane, chlorobenzene or a dichlorobenzene), a lower alcohol chosen from $C_1$-$C_4$ alkanols and more particularly methanol or ethanol, or a mixture of these solvents.

When the oxidising agent chosen is m-CPBA, the process is preferably performed in a mixture of ethanol and dichloromethane.

It is possible to control the degree of oxidation of the final compound by varying the amount of equivalents of oxidising agent used.

In order to prepare compounds of the formula I in which n=1, the compound of the formula Ia will be placed in contact with not more than about one equivalent of m-CPBA (preferably between 0.9 and 1.1 equivalents).

In order to prepare compounds of the formula I in which n=2, use will be made of at least about 2 equivalents of m-CPBA.

The reaction is advantageously performed at a moderate temperature of between 15 and 40° C., for example at room temperature, when the oxidising agent is m-CPBA.

D) Preparation of the Compounds of the Formula I in which A Represents Alkyloxycarbonyl or Aryloxycarbonyl The compounds of the formula I in which A represents —COOH may be readily converted into compounds of the formula I in which A represents alkoxycarbonyl or aryloxycarbonyl by reaction with the corresponding alkyl alcohol or aryl alcohol, respectively.

According to one preferred embodiment of the invention, it is an active derivative of the carboxylic acid of the formula I in which A=COOH that is reacted with the alkyl alcohol or the aryl alcohol, respectively.

The activated derivative of the carboxylic acid is the corresponding compound of the formula I in which A=—CO—K in which K is an activating group for the carboxylic acid function.

Preferred activating groups that may be mentioned include chlorine, bromine, azide, imidazolide, p-nitrophenoxy, 1-benzotriazole, N—O-succinimide, acyloxy and more particularly pivaloyloxy, ($C_1$-$C_4$ alkoxy)carbonyloxy such as $C_2H_5CO$—O—, and dialkyl- or dicydoalkyl-O-ureide.

When K=OH, the reaction of the compound of the formula I in which A=—COOH with the alkyl alcohol or aryl alcohol, respectively, is preferably performed in the presence of a coupling agent such as a carbodiimide, optionally in the presence of an activating agent such as hydroxybenzotriazole or hydroxysuccinimide with the intermediate formation of dialkyl- or dicycloalkyl-O-ureides. Representative coupling agents are dicyclohexyl- and diisopropylcarbodiimides, carbodiimides that are soluble in an aqueous medium, or bis(2-oxo-3-oxazolidinyl)phosphonyl chloride.

When K is a halogen atom, it is desirable to perform the process in the presence of a mineral or organic base such as, for example, a hydroxide (such as an ammonium or alkali metal hydroxide), a carbonate (such as an alkali metal or alkaline-earth metal carbonate), an alkali metal alkoxide, an alkali metal amide, ammonia, triethylamine, tributylamine, pyridine or N-methylmorpholine.

Another suitable base that may be used is a base supported on resin. Resins of this type are commercially available.

Examples that may be mentioned include N,N-(diisopropyl)aminomethylpolystyrene and morpholinomethylpolystyrene resins.

The reaction is preferably performed in a solvent.

In certain cases, the base can serve as solvent. This case, for example, for pyridine.

As a variant, it is advantageous to select a polar aprotic solvent, and for example a halogenated hydrocarbon such as methylene chloride, chloroform, carbon tetrachloride, dichloroethane, chlorobenzene or a dichlorobenzene, dichloroethane being particularly preferred.

E) Preparation of the Compounds of the Formula I in which A Represents —CONH—OH

The compounds of the formula I in which A represents CONH—OH may be obtained from the corresponding compounds of the formula I in which A represents —COOH by the action of hydroxylamine, this reaction being performed in a manner that is known per se, using known techniques of organic chemistry.

According to one particularly preferred embodiment of the invention, this reaction is performed in two steps.

In a first step, the function A=COOH is activated. To do this, any activated carboxylic acid derivative may be prepared (formula I in which A=—COK) described above in step D.

Preferably, the activated derivative is an acid chloride, a carbodiimide or a mixed anhydride.

In a second step, the said activated derivative is reacted with hydroxylamine in the presence of a base, for example one of the bases defined in step D above. Advantageously, the base is triethylamine or N-methylmorpholine.

This step is preferably performed in a polar aprotic solvent such as a halogenated hydrocarbon (and especially dichloromethane), an ether (and especially tetrahydrofuran) or an amide (and especially dimethylformamide).

F) Preparation of the Compounds of the Formula I in which A Represents Tetrazolyl The compounds of the formula I in which A represents tetrazolyl are readily prepared from the corresponding compounds of the formula I in which A represents —COOH by carrying out a two-step process.

In a first step, the corresponding amide of the formula IX is prepared:

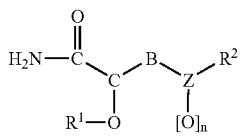

from the carboxylic acid of the formula Ib below:

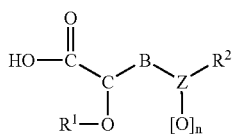

in which $R^1$, B, Z, n and $R^2$ are as defined above for formula I.

The conversion of compound Ib into an amide may be performed in any manner, and for example by the action:

a- of ammonia in methanol in the presence of a Dowex 50W×8 resin;
b- of ethyl chloroformate and ammonia;
c- of $SO_2(NH_2)_2$ in pyridine; or
d- of thionyl chloride and ammonium hydroxide in 1,4-dioxane.

In a second step, the amide of the formula IX is reacted with an alkali metal azide (such as sodium azide), in the presence of tetrachlorosilane.

This step is performed, for example, in a nitrile as solvent, such as acetonitrile or isobutyronitrile, preferably acetonitrile.

To establish the operating conditions, a person skilled in the art may refer to the studies by El-Ahl, A. A. S; Elmorsy S. S. et al. published in Tetrahedron Letters, 1997, 38(7), 1257.

The lactones of the formula II:

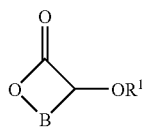

in which B and $R^1$ are as defined above for formula I may be obtained by reacting a corresponding α-halolactone of the formula V:

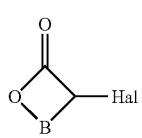

in which Hal represents a halogen atom preferably chosen from chlorine, bromine and iodine (bromine being more particularly preferred), with the appropriate alcohol of the formula VI:

$R^1$—OH                                           VI in the presence of an organic or mineral base.

As a variant, it is possible to synthesise the intermediate compounds of the formula II by the action of the corresponding α-hydroxylactone of the formula VII:

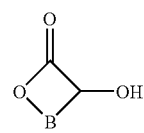

on the appropriate halide of the formula VIII:

$R^1$-Hal                                           VIII in which formulae $R^1$ and B are as defined for formula I and Hal is a halogen atom preferably chosen from chlorine, bromine and iodine (bromine being more particularly preferred), this reaction being performed in the presence of an organic or mineral base.

The bases that may be used in the preparation of compounds of the formula II are those generally defined above.

In the case of the first variant (reaction of V with VI), it is preferred to use an alkali metal carbonate (such as caesium carbonate) or an alkali metal alkoxide (such as sodium ethoxide) as base.

In the case of the second variant, a base such as an alkali metal hydride and especially sodium hydride is particularly suitable.

The operating conditions, and especially the reaction temperature and the solvent, depend especially on the type of base used.

In the first variant (reaction of V with VI), the process is preferably performed:

either in a ketone (such as acetone), in the presence of an alkali metal carbonate such as caesium carbonate, at a temperature of between 40 and 100° C. and better still between 50 and 70° C.;

or in a lower alcohol (such as a $C_1$-$C_4$ alkanol of the type such as ethanol) in the presence of the corresponding alkali metal alkoxide, at a temperature of between 40 and 120° C., for example between 50 and 100° C. and more particularly between 60 and 80° C.

In the second variant, preferred conditions are the use of an alkali metal hydride such as a sodium hydride, the choice of an amide as solvent and advantageously dimethylformamide, at a temperature ranging between −5 and 45° C. According to one preferred embodiment of the invention, the base is reacted with the α-hydroxylactone at low temperature (between −5 and +10° C.), followed by addition to the reaction medium of the halide of the formula VIII, leaving it to react at a temperature generally of between 15 and 45° C., for example at room temperature, for the time required for the reaction.

The enantiomers of the compounds of the formula I that contain an asymmetric carbon a to the group A:

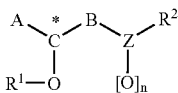

*denoting the position of the asymetric centre, may be prepared from the corresponding enantiomeric lactones of the formula II:

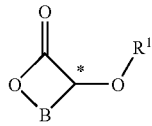

in which the carbon labelled with the asterisk has the same configuration as the corresponding carbon in formula Ib above, by carrying out the same type of reaction as described above in A).

One method for preparing the optically active compounds of the formula II is as follows.

The alcohol of the formula VI, $R_1OH$, is reacted with an optically active α-hydroxylactone of the formula VIIa:

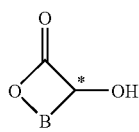

in which B is as defined above for formula I in the presence of diethyl azodicarboxylate and triphenylphosphine.

Ideally, the reaction is carried out in a polar aprotic solvent such as an ether of the type such as diethyl ether, diisopropyl ether, tetrahydrofuran, dioxane, dimethoxyethane or diethylene glycol dimethyl ether. As a variant, a halogenated hydrocarbon such as methylene chloride, chloroform, carbon tetrachloride, dichloroethane, chlorobenzene or a dichlorobenzene may be used.

Since this reaction takes place with inversion of stereochemistry at the endocydic asymmetric carbon, bearing the —OH group, the o-hydroxylactone of the formula VIIa, which is of opposite configuration relative to the configuration of the corresponding carbon in formula II, will be selected.

Schematically:

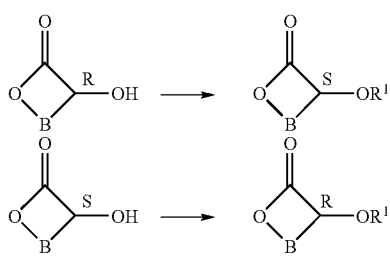

The invention also relates to pharmaceutical compositions comprising a pharmaceutically effective amount of a compound of the formula (I) as defined above in combination with one or more pharmaceutically acceptable vehicles.

These compositions may be administered orally in the form of tablets, gel capsules or granules with immediate release or sustained release, intravenously in the form of an injectable solution, transdermally in the form of an adhesive transdermal device, or locally in the form of a solution, cream or gel.

The pharmaceutical compositions of the present invention may also be administered by nasal aerosol or inhalation through the use of a nebulizer, a dry powder inhaler or a metered dose inhaler. Such compositions are prepared according to techniques well-known in the art of pharmaceutical formulation and may be prepared as solutions in saline, employing benzyl alcohol or other suitable preservatives, absorption promoters to enhance bioavailability, hydrofluorocarbons, and/or other conventional solubilizing or dispersing agents.

A solid composition for oral administration is prepared by adding to the active principle a filler and, where appropriate, a binder, a disintegrating agent, a lubricant, a colorant or a flavour enhancer, and by placing the mixture in the form of a tablet, a coated tablet, a granule, a powder or a capsule.

Examples of fillers include lactose, corn starch, sucrose, glucose, sorbitol, crystalline cellulose and silicon dioxide, and examples of binders include poly(vinyl alcohol), poly (vinyl ether), ethylcellulose, methylcellulose, acacia, gum tragacanth, gelatin, shellac, hydroxypropylcellulose, hydroxypropylmethylcellulose, calcium citrate, dextrin and pectin. Examples of lubricants include magnesium stearate, talc, polyethylene glycol, silica and hardened plant oils. The colorant may be any of those permitted for used in medicaments. Examples of flavour enhancers include cocoa powder, mint in herb form, aromatic powder, mint in oil form, borneol and cinnamon powder. Obviously, the tablet or granule may be suitably coated with sugar, gelatin or the like.

An injectable form containing the compound of the present invention as active principle is prepared, where appropriate, by mixing the said compound with a pH regulator, a buffer agent, a suspension agent, a solubiliser, a stabiliser, an isotonic agent and/or a preserving agent, and by converting the mixture into a form for intravenous, subcutaneous or intramuscular injection, according to a standard process. Where appropriate, the injectable form obtained may be freeze-dried by a standard process.

Examples of suspension agents include methylcellulose, polysorbate 80, hydroxyethylcellulose, acacia, powdered gum tragacanth, sodium carboxymethylcellulose and polyethoxylated sorbitan monolaurate.

Examples of solubilisers include castor oil solidified with polyoxyethylene, polysorbate 80, nicotinamide, polyethoxylated sorbitan monolaurate and the ethyl ester of castor oil fatty acid.

In addition, the stabiliser encompasses sodium sulphite, sodium metasulphite and ether, while the preserving agent encompasses methyl p-hydroxybenzoate, ethyl p-hydroxybenzoate, sorbic acid, phenyl [sic], cresol and chlorocresol.

The invention is also directed towards the use of an active principle chosen from a compound of the formula (I) as defined above, for the preparation of a medicament intended for preventing or treating dyslipidaemia, atherosclerosis and diabetes.

In the above description of pharmaceutical compositions containing a preferred compound, the equivalent expressions: "administration", "administration of", "administering", and "administering a" have been used with respect to said pharmaceutical compositions. As thus employed, these expressions are intended to mean providing to a patient in need of treatment a pharmaceutical composition of the present invention by any of the routes of administration herein described, wherein the active ingredient is a preferred compound or a prodrug, derivative, or metabolite thereof which is useful in treating a disease, disorder, or condition mediated by or associated with modulation of activation of PPARα and PPARγ isoforms in said patient. Accordingly, there is included within the scope of the present invention any other compound which, upon administration to a patient, is capable of directly or indirectly providing a preferred compound. Such compounds are recognized as prodrugs, and a number of established procedures are available for preparing such prodrug forms of the preferred compounds.

The dosage and dose rate of the compounds effective for treating or preventing, a disease, disorder, or condition mediated by or associated with modulation of activation of PPARα and PPARγ isoforms, will depend on a variety of factors, such as the nature of the activator, the size of the patient, the goal of the treatment, the nature of the pathology to be treated, the specific pharmaceutical composition used, and the observations and conclusions of the treating physician.

For example, where the dosage form is oral, e.g., a tablet or capsule, suitable dosage levels of the compounds of formula I will be between about 0.1 μg/kg and about 50.0 mg/kg of body weight per day, preferably between about 5.0 μg/kg and about 5.0 mg/kg of body weight per day, more preferably between about 10.0 μg/kg and about 1.0 mg/kg of body weight per day, and most preferably between about 20.0 μg/kg and about 0.5 mg/kg of body weight per day of the active ingredient.

Where the dosage form is topically administered to the bronchia and lungs, e.g., by means of a powder inhaler or nebulizer, suitable dosage levels of the compounds will be between about 0.001 μg/kg and about 10.0 mg/kg of body weight per day, preferably between about 0.5 μg/kg and about 0.5 mg/kg of body weight per day, more preferably between about 1.0 μg/kg and about 0.1 mg/kg of body weight per day, and most preferably between about 2.0 μg/kg and about 0.05 mg/kg of body weight per day of the active ingredient.

Using representative body weights of 10 kg and 100 kg in order to illustrate the range of daily oral dosages which might be used as described above, suitable dosage levels of the compounds of formula I will be between about 1.0-10.0 μg and 500.0-5000.0 mg per day, preferably between about 50.0-500.0 μg and 50.0-500.0 mg per day, more preferably between about 100.0-1000.0 μg and 10.0-100.0 mg per day, and most perferably between about 200.0-2000.0 μg and about 5.0-50.0 mg per day of the active ingredient comprising a preferred compound. These ranges of dosage amounts represent total dosage amounts of the active ingredient per day for a given patient. The number of times per day that a dose is administered will depend upon such pharmacological and pharmacokinetic factors as the half-life of the active ingredient, which reflects its rate of catabolism and clearance, as well as the minimal and optimal blood plasma or other body fluid levels of said active ingredient attained in the patient which are required for therapeutic efficacy.

The activity of the compounds of the invention leading to a hypolipidaemiant and hypoglycaemiant effect was demonstrated in vitro and in vivo by carrying out the following tests.

The measurement of the PPAR activation was performed according to a technique described by Lehmann et al. (1995, J. Biol. Chem. 270: 12953-12956).

CV-1 cells (monkey kidney cells) are co-transfected with an expression vector for the chimeric proteins PPARα-Gal4 or PPARγ-Gal4 and with a "reporter" plasmid which allows the expression of the luciferase gene placed under the control of a promoter containing Gal4 response elements.

The cells are inoculated in 96-zwell microplates and co-transfected using a commercial reagent with the reporter plasmid (pG5-tk-pGL3) and the expression vector for the chimeric protein (PPARα-Gal4 or PPARγ-Gal4). After incubating for 4 hours, whole culture medium (containing 10% foetal calf serum) is added to the wells. After 24 hours, the medium is removed and replaced with whole medium containing the test products (50 μM final). The products are left in contact with the cells for 18 hours. The cells are then lysed and the ludferase activity is measured using a luminometer. A PPAR activation factor can then be calculated by means of the activation of the expression of the reporter gene induced by the product (relative to the control cells that have not received any product).

By way of example, the compound of Example 5, at a concentration of 50 μM, activates the chimeric protein PPARα-Gal-4 by factor of nine, and the chimeric protein PPARγ-Gal4 by a factor of six. In the absence of the binding region for the PPARα or γ ligand (vector expressing Gal4 alone), the luciferase activity measured in the presence of this product is zero.

The antidiabetic and hypolipidaemiant activity of the compounds was determined orally in db/db mice.

16 week-old db/db mice are treated orally for 15 days with the compound of Example 5 (20 mg/kg/day). Each group studied comprises seven animals. After treatment for 15 days, retro-orbital samples are taken after a mild anaesthesia and fasting for 4 hours.

The following parameters were measured:

Glycaemia assay (glucose oxidase) and assay of the lipid parameters on the sera at D15 (COBAS): triglycerides, total cholesterol (CHOL), the HDL cholesterol (HDL-C) and the free fatty acids (FFA) (BioMérieux and Waco Chemicals assay kit).

The results obtained are collated in the following table. The measurements given represent mean values±standard error.

|  | Control | Example 5 | % variation relative to the control |
|---|---|---|---|
| Glycaemia mM | 27.1 ± 7.0 | 11.1 ± 3.3 | −59* |
| Triglycerides mM | 1.3 ± 0.3 | 0.7 ± 0.1 | −47* |
| HDL-C mM | 3.2 ± 0.2 | 4.3 ± 0.6 | 36* |
| CHOL mM | 3.65 ± 0.2 | 5.4 ± 0.9 | 47* |
| FFA mM | 0.7 ± 0.1 | 0.4 ± 0.0 | −38* |

% var: percentage of variation versus control.
Mann-Whitney Test: *, p < 0.05 vs control These results demonstrate the antidiabetic and hypolipidaemiant activity of the compounds of the invention on triglycerides and free fatty acids. The marked increase in the level of HDL cholesterol by these same compounds should be noted.

The examples that follow illustrate invention in a non-limiting manner.

In the proton nuclear magnetic resonance data (300 MHz NMR), the following abbreviations have been used: s for singlet, d for doublet, t for triplet, q for quartet, o for octet and

Preparation 1:
3-(4-fluorophenoxy)dihydrofuran-2-one

α-Bromobutyrolactone (12.4 g, 0.075 mol) is added to a mixture of 4-fluorophenol (5.6 g, 0.05 mol) and caesium carbonate (17.9 g, 0.055 mol) in acetone (100 ml). The reaction medium is refluxed for two hours. After cooling to room temperature, the reaction is filtered through a bed of Celite and the filtrate is evaporated. The oily residue is purified by flash chromatography (1/2 EtOAc/heptane) to give the expected product in the form of an oil (9.8 g, 87%).

$^1$H NMR (CDCl$_3$, 300 MHz): 2.4 (1H, m), 2.65 (1H, m), 4.3 (1H, m), 4.8 (1H, m), 4.8 (1H, t, J=7.5 Hz), 6.95 (4H, m).

Preparation 2:
3-(4-bromophenoxy)dihydrofuran-2-one

Sodium (23 g, 1 mol) is added in pieces to a reactor containing ethanol (1 l). The temperature of the reaction medium is stabilised at 70° C. (exothermic) before adding a solution of 4-bromophenol (173 g, 1 mol) in ethanol (150 ml). After cooling to room temperature, α-bromo-γ-butyrolactone (83 ml, 1 mol) is added slowly. The reaction medium is stirred for ten hours and is then treated by adding 1N hydrochloric acid solution (600 ml). The aqueous phase is extracted with ethyl acetate (2×1 l) and the combined organic phases are washed with water (1 l), dried over sodium sulphate, filtered and concentrated. The residue obtained is recrystallised from isopropanol (2.2 l) to give the expected compound in the form of a white powder (80.1 g, 31%).

m.p: 90° C. IR: 1690, 1770, 1790. $^1$H NMR (CDCl$_3$, 300 MHz): 2.5 (1H, m), 2.7 (1H, m), 4.4 (1H, m), 4.5 (1H, m), 4.9 (1H, t, J=7.5 Hz), 6.9 (2H, m), 7.4 (2H, m).

Preparation 3:
3-(4-trifluoromethylphenoxy)dihydrofuran-2-one

The compound is prepared according to the experimental procedure described in Preparation 1, starting with α-bromo-γ-butyrolactone (6.7 g, 0.040 mol) and 4-trifluoromethylphenol (5.0 g, 0.031 mol) to give 3.51 g of the expected compound in the form of a white powder.

m.p.: 84-86° C.; $^1$H NMR (DMSO-d6, 300 MHz): 2.20-2.45 (1H, m), 2.70-2.90 (1H, m), 4.20-4.53 (2H, m), 5.51 (1H, t, J=9.0 Hz), 7.74 (2H, d, J=8.9 Hz), 7.69 (2H, d, J=8.9 Hz).

Preparation 4:
3-(biphenyl-2-ylmethoxy)dihydrofuran-2-one

Sodium hydride (0.43 g, 10.8 mmol) is added portionwise to a solution of α-hydroxy-γ-butyrolactone (1 g, 9.8 mmol) in DMF (15 ml) at 0° C. under a nitrogen atmosphere. 2-Bromomethylbiphenyl (2.42 g, 9.8 mmol) is then rapidly added. The reaction medium is stirred for 2 hours at room temperature and is then treated by adding 1N hydrochloric acid solution (10 ml). The aqueous phase is extracted with ethyl acetate (2×20 ml) and the combined organic phases are washed with water (4×15 ml), dried over sodium sulphate, filtered and concentrated. After purification by flash chromatography (2/1 heptane/EtOAc), the expected compound is obtained in the form of a colourless oil (1.32 g, 50%).

$^1$H NMR (CDCl$_3$, 300 MHz): 2.00-2.35 (2H, m), 3.85-4.00 (1H, m), 4.00-4.15 (1H, m), 4.15-4.30 (1H, m), 4.40-4.80 (2H, m), 7.10-7.40 (8H, m), 8.40-8.60 (1H, m).

Preparation 5:
(S)-3-(4-trifluoromethylphenoxy)dihydrofuran-2-one

Diethyl azodicarboxylate (2.31 ml, 14.7 mmol) is slowly added to a solution of (R)-(+)-α-hydroxy-γ-butyrolactone (1 g, 9.8 mmol), 4-trifluoromethylphenol (1.58 g, 9.8 mmol) and triphenylphosphine (3.86 g, 14.7 mmol) in anhydrous THF (80 ml) cooled to 0° C. After stirring for 5 minutes at 0° C. and overnight at room temperature, the solvent is evaporated off and the triphenylphosphine oxide is then precipitated from ether and filtered off. The filtrate is then washed with water, dried over magnesium sulphate and evaporated. After purification by flash chromatography (3/1 heptane/EtOAc), the expected compound is obtained in the form of a white powder (1.14 g, 47%).

$^1$H NMR (DMSO-d6, 300 MHz): 2.20-2.45 (1H, m), 2.70-2.90 (1H, m), 4.20-4.53 (2H, m), 5.51 (1H, t, J=9.0 Hz), 7.74 (2H, d, J=8.9 Hz), 7.69 (2H, d, J=8.9 Hz).

Preparation 6:
(R)-3-(4-trifluoromethylphenoxy)dihydrofuran-2-one

The compound is prepared according to the experimental procedure described, starting with (S)-(−)-α-hydroxy-γ-butyrolactone (2 g, 19.6 mmol) and 4-trifluoroethylphenol (3.18 g, 19.6 mmol) to give 1.7 g (35%) of the expected compound in the form of a white powder.

$^1$H NMR (DMSO-d6, 300 MHz): 2.20-2.45 (1H, m), 2.70-2.90 (1H, m), 4.20-4.53 (2H, m), 5.51 (1H, t, J=9.0 Hz), 7.74 (2H, d, J=8.9 Hz), 7.69 (2H, d, J=8.9 Hz).

EXAMPLE 1
2-(4-fluorophenoxy)-4-phenylsulphanylbutyric acid

A 1 N solution of sodium tert-butoxide in DMF (0.2 ml, 0.2 mmol) is added to a solution of thiophenol (25 mg, 0.23 mmol) in DMF (1 ml). After stirring for 15 minutes at room temperature, a solution of preparation 1 (30 mg, 0.15 mmol) in DMF (1 ml) is added and the mixture is heated at 120° C. for 1 hour. After cooling to room temperature, the reaction is treated with 1N hydrochloric add (1 ml) and the product is extracted with ethyl acetate (3 ml). The organic phase is washed with water (3×2 ml) and is then concentrated until a volume of 1 ml is obtained. This solution is purified by flash chromatography (2/1 heptane/EtOAc) to give the expected compound in the form of a white powder (27 mg, 57%).

$^1$H NMR (CDCl$_3$, 300 MHz): 2.35 (2H, m), 3.0 (2H, m), 4.7 (1H, dd, J=9.5 Hz), 6.75 (1H, m), 6.95-6.8 (3H, m), 7.0 (2H, m); MS AP$^-$ (M−1)=305.

EXAMPLE 2
2-(4-bromophenoxy)-4-o-tolylsulphanylbutyric acid

The compound is prepared according to the experimental procedure described in Example 1, starting with the compound of preparation 2 (2 g, 7.8 mmol) and ortho-thiocresol (1.38 ml, 11.6 mmol) to give the compound of Example 2 in the form of an oil that crystallises on standing (2.3 g, 77%).

m.p.: 96-98° C.; $^1$H NMR (CDCl$_3$, 300 MHz): 2.2 (2H, m), 2.3 (3H, s), 3.1 (2H, m), 4.8 (1H, dd, J=3.5 and 9.5), 6.7 (2H, m), 7.1 (2H, m), 7.2 (2H, m), 7.3 (2H, d, J=9 Hz).

EXAMPLE 3

4-o-tolylsulphanyl-2-(4-trifluoromethylphenoxy) butyric add

The compound is prepared according to the experimental procedure described in Example 1, starting with the compound of preparation 3 (6.7 g, 0.040 mol) and ortho-thiocresol (1.38 ml, 11.6 mmol) to give 3.51 g of the expected compound in the form of a white powder.

$^1$H NMR (CDCl$_3$, 300 MHz): 2.20-2.50 (3H, s+2H, m); 3.00-3.25 (2H, m); 4.94 (1H, m); 6.85-7.00 (2H, m); 7.00-7.20 (3H, m); 7.20-7.40 (1H, m) 7.50-7.65 (2H, m), (N.B.: acid OH not observed).

EXAMPLE 4

2-(biphenyl-2-ylmethoxy)-4-phenylsulphanylbutyric acid

Sodium hydride (60% dispersion) (12 mg, 0.9 mmol) is added to a solution of thiophenol (100 mg, 0.9 mmol) in DMF (1 ml) at room temperature. After stirring for 30 minutes, a solution of the compound of preparation 4 (52 mg, 0.2 mmol) in DMF (1 ml) is added and the temperature of the reaction medium is maintained at 120° C. for 3 hours. After cooling to room temperature, the reaction is treated with 1N hydrochloric acid (2 ml) and the product is extracted with ethyl acetate (3 ml). The organic phase is washed with water (3×3 ml) and is then dried over magnesium sulphate, filtered and evaporated. After purification by flash chromatography (heptane), the expected compound is obtained in the form of a colourless oil (50 mg, 69%).

$^1$H NMR (DMSO-d6, 300 MHz): 1.80-2.00 (2H, m); 2.85-3.10 (2H, m); 3.95 (1H, m); 4.20-4.60 (2H, m); 7.10-7.30 (6H, m); 7.30-7.50 (7H, m); 7.50-7.60 (1H, m); 12.83 (1H, exchangeable, broad s).

EXAMPLE 5

4-phenylsulphanyl-2-(4-trifluoromethylphenoxy) butyric acid

The compound is prepared according to the experimental procedure described for Example 1, starting with the compound of preparation 3 (6.7 g, 0.040 mol) and thiophenol (1.38 ml, 11.6 mmol) to give 3.51 g of the expected compound in the form of a white powder.

m.p.: 108-110° C.; $^1$H NMR (DMSO-d6, 300 MHz): 2.10-2.30 (2H, m); 3.00-3.20 (2H, m); 5.00 (1H, m); 7.00-7.10 (2H, m); 7.10-7.60 (5H, m); 7.60-7.80 (2H, m); 13.35 (1H, exchangeable, broad s); MS AP− (M−1)=355.

EXAMPLE 6

4-phenylselanyl-2-(4-trifluoromethylphenoxy)butyric acid

Sodium borohydride (30 mg, 0.8 mmol) is added to a solution of diphenyl diselenide (111 mg, 0.35 mmol) in DMF (1.5 ml) at room temperature. The mixture is heated at 100° C. for 20 minutes, followed by addition of a solution of the compound of preparation 3 (160 mg, 0.65 mmol) in DMF (1 ml). The reaction mixture is then heated at 120° C. for 2.5 hours. After cooling to room temperature, the reaction medium is treated with 10% hydrochloric acid (1 ml) and the product is extracted with ethyl acetate (4 ml). The organic phase is washed with water (3×2 ml) and is then dried over magnesium sulphate, filtered and evaporated. After purification by flash chromatography (2/1 heptane/EtOAc), the expected compound is obtained in the form of a white powder (176 mg, 67%).

$^1$H NMR (CDCl$_3$, 300 MHz): 2.20-2.55 (2H, m); 2.90-3.30 (2H, m); 4.92 (1H, m); 6.80-7.00 (2H, m); 7.10-7.30 (3H, m); 7.40-7.60 (4H, m); (N.B.: acid OH not observed).

EXAMPLE 7

Methyl 4-(toluene-2-sulphanyl)-2-(4-trifluoromethylphenoxy)butyrate

A catalytic amount of H$_2$SO$_4$ (2 drops) is added to a solution of the compound of Example 3 (5.14 g, 13.9 mmol) in methanol (40 ml). The reaction is refluxed for 12 hours. The solvent is then evaporated off under vacuum, the residue is taken up in ethyl acetate (50 ml) and the organic phase is washed with water (2×50 ml), dried over sodium sulphate, filtered and concentrated. After purification by flash chromatography (1/5 EtOAc/heptane), the compound of Example 7 is obtained in the form of a yellow oil (5 g, 93%).

$^1$H NMR (CDCl$_3$): 2.11-2.44 (5H, m); 2.96-3.21 (2H, m); 3.74 (3H, s); 4.80-4.97 (1H, m); 6.84-6.97 (2H, m); 7.03-7.33 (4H, m); 7.47-7.58 (2H, m).

EXAMPLE 8

4-o-tolylsulphanyl-2-(S)-(4-trifluoromethylphenoxy) butyric acid

Caesium carbonate is added to a solution of ortho-thiocresol (66 mg, 0.53 mmol) in anhydrous DMF (1 ml) under nitrogen. After stirring for 15 minutes at room temperature, a solution of the compound of preparation 5 (100 mg, 0.4 mmol) in anhydrous DMF (1 ml) is added and the reaction medium is heated at 120° C. for one hour. After cooling to room temperature, the reaction is treated with 1N hydrochloric acid (1 ml) and the product is extracted with ethyl acetate (3 ml). The organic phase is washed with water (3×2 ml) and is then concentrated until a volume of 1 ml is obtained. This solution is purified by flash chromatography (2/1 heptane/EtOAc) to give the compound of Example 8 in the form of a white powder (93 mg, 62%).

$[\alpha]_D = -32.5$ (c=0.5, MeOH)

$^1$H NMR (CDCl$_3$, 300 MHz): 2.20-2.50 (3H, s+2H, m); 3.00-3.25 (2H, m); 4.94 (1H, m); 6.85-7.00 (2H, m); 7.00-7.20 (3H, m); 7.20-7.40 (1H, m) 7.50-7.65 (2H, m) (N.B.: acid OH not observed).

EXAMPLE 9

4-o-Tolylsulphanyl-2-(R)-(4-trifluoromethylphenoxy)butyric acid

The compound is prepared according to the experimental procedure described for Example 8, starting with the compound of preparation 6 (100 mg, 0.4 mmol) and ortho-thiocresol (66 mg, 0.53 mmol) to give 90 mg of the expected compound in the form of a white powder.

$[\alpha]_D = +33.0$ (c=0.5, MeOH) $^1$H NMR (CDCl$_3$, 300 MHz): 2.20-2.50 (3H, s+2H, m); 3.00-3.25 (2H, m); 4.94 (1H, m);

6.85-7.00 (2H, m); 7.00-7.20 (3H, m); 7.20-7.40 (1H, m); 7.50-7.65 (2H, m) N.B.: acid OH not observed.

EXAMPLE 10

Methyl 4-(toluene-2-sulphonyl)-2-(4-trifluoromethylphenoxy)butyrate

70% MCPBA (1.49 g, 3.9 mmol) is added to a solution of the compound of Example 7 (500 mg, 1.3 mmol) in $CH_2Cl_2$ (10 ml) at 0° C. The reaction is stirred at room temperature for one hour. The reaction is then diluted with $CH_2Cl_2$ (10 ml) and poured into saturated sodium bisulphite solution (20 ml). The organic phase is washed with saturated $NaHCO_3$ solution (2×20 ml), $H_2O$ (20 ml), dried over sodium sulphate, filtered and concentrated. The compound of Example 10 is obtained in the form of a colourless oil (540 mg, 99%).

$^1$H NMR ($CDCl_3$): 2.21-2.59 (2H, m); 2.67 (3H, s); 3.21-3.51 (2H, m); 3.74 (3H, s); 4.73-4.95 (1H, m); 6.72-6.95 (2H, m); 7.26-7.62 (5H, m); 7.79-8.09 (1H, m), MS ES+(M+1)=417

EXAMPLE 11

Methyl 4-(toluene-2-sulphinyl)-2-(4-trifluoromethylphenoxy)butyrate

A 13% sodium hypochlorite solution (0.246 ml, 0.250 mmol) is added to a solution of the compound of Example 7 (200 mg, 0.520 mmol) in methanol (4 ml) at −78° C. The reaction is stirred at −78° C. for 1 hour. The methanol is then evaporated off, the residue is taken up in ethyl acetate (5 ml) and the organic phase is washed with 1N hydrochloric acid solution (3 ml), with water (3 ml), filtered through a filter membrane (porosity 5 μm) and concentrated. After purification by flash chromatography (1/2 EtOAc/heptane and then 1/2/2 MeOH/EtOAc/heptane), the compound of Example 11 is obtained in the form of a colourless amorphous product (60 mg, 29%).

$^1$H NMR ($CDCl_3$): 1.93-2.70 (5H, m); 2.70-3.22 (2H, m); 3.73 and 3.75 (3H, 2s); 4.65-4.99 (1H, m); 6.72-7.04 (2H, m); 7.07-7.63 (5H, m); 7.75-8.00 (1H, m), MS ES+(M+1)=401

EXAMPLE 12

4-(Toluene-2-sulphonyl)-2-(4-trifluoromethylphenoxy)butyric acid

A 1N sodium hydroxide solution (0.7 ml, 0.7 mmol) is added dropwise to a solution of the compound of Example 10 (220 mg, 0.53 mmol) in THF (5 ml) at 0° C. The reaction is stirred at room temperature for 1 hour. The THF is evaporated off; the residue is taken up in ethyl acetate (5 ml) and the organic phase is washed with 1N hydrochloric acid solution (3 ml), with water (4 ml), dried over sodium sulphate, filtered and evaporated to give the compound of Example 12 (210 mg, 99%) in the form of a colourless amorphous product.

$^1$H NMR ($CDCl_3$): 2.29-2.70 (5H, m); 3.22-3.54 (2H, m); 4.76-5.01 (1H, m); 6.54 (1H, broad s); 6.78-6.97 (2H, m); 7.19-7.43 (2H, m); 7.43-7.63 (3H, m); 7.87-8.08 (1H, m), MS ES−(M−1)=401

EXAMPLE 13

4-(Toluene-2-sulphinyl)-2-(4-trifluoromethylphenoxy)butyric acid

A 1N sodium hydroxide solution (0.2 ml, 0.2 mmol) is added dropwise to a solution of the compound of Example 11 (60 mg, 0.12 mmol) in ThF (2 ml) at 0° C. The reaction is stirred at room temperature for 1 hour and then at 50° C. for a further one hour. The THF is evaporated off; the residue is taken up in ethyl acetate (5 ml) and the organic phase is washed with 1N hydrochloric acid solution (3 ml), with water (4 ml), dried over sodium sulphate, filtered and evaporated to give the compound of Example 12 (210 mg, 99%) in the form of a colourless amorphous product.

$^1$H NMR ($CDCl_3$): 2.06-2.69 (5H, m); 2.87-3.32 (2H, m); 4.67-5.15 (1H, m); 5.80 (1H, broad s); 6.81-7.04 (2H, m); 7.14-7.33 (1H, m); 7.33-7.60 (4H, m); 7.79-7.99 (1H, m), MS ES−(M−1)=385

Synthesis of compounds from examples 10-13 is outlined in the following scheme:

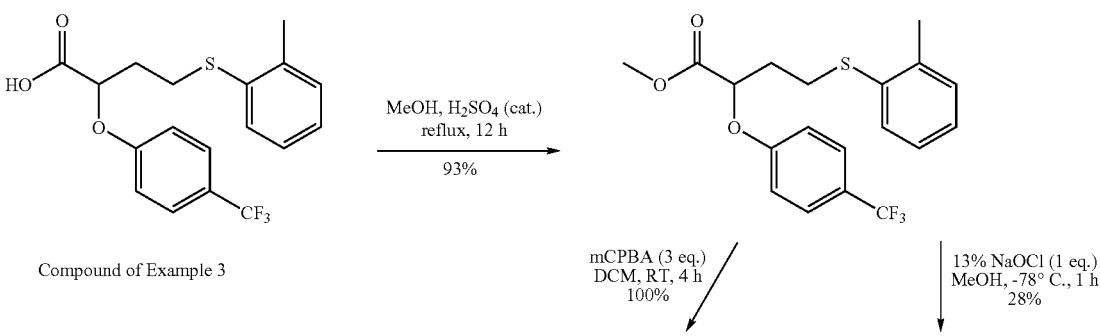

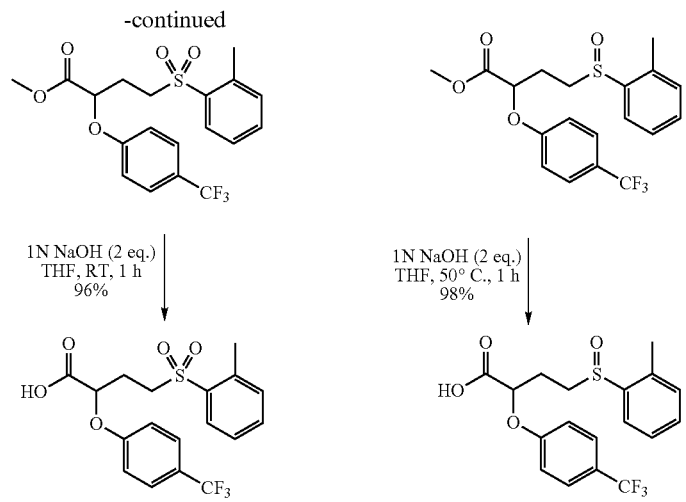

Table I below illustrates Examples 10 to 60, which are compounds of the formula I in which A represents —COOH and B represents —CH$_2$—CH$_2$.

TABLE 1

| Ex. | R$^1$ | R$^2$ | Z | n | Characterisation data |
|---|---|---|---|---|---|
| 1 | p-fluorophenyl | phenyl | S | 0 | CDCl$_3$: 2.35(2H, m), 3.0 (2H, m), 4.7(1H, dd, J=9.5 Hz), 6.75(1H, m), 6.95-6.8 (3H, m), 7.0(2H, m), |
| 2 | p-bromophenyl | 2-methylphenyl | S | 0 | CDCl$_3$: 2.15-2.20(3H, s+2H.m); 3.00-3.25(2H, m); 4.82(1H, m); 6.70-6.90(2H, m); 7.00-7.50(6H, m)(N.B.: acid OH not observed) |
| 3 | 4-trifluoromethyl-phenyl | 2-methylphenyl | S | 0 | DMSO-d6: CDCl$_3$: 2.20-2.50(5H, m); 3.00-3.25(2H, m); 4.94(1H, m); 6.90-7.00 (2H, m); 7.00-7.20(3H, m); 7.20-7.35(1H.m); 7.45-7.65 (2H.m)(N.B.: acid OH not observed) |
| 4 | o-phenylbenzyl | phenyl | S | 0 | DMSO-d6: 1.80-2.00(2H, m); 2.85-3.10(2H, m); 3.95 (1H, m); 4.20-4.60(2H, m); 7.10-7.30(6H.m); 7.30-7.50 (7H, m); 7.50-7.60(1H, m); 12.83(1H, exchangeable, broad s) |
| 5 | 4-trifluoromethyl-phenyl | phenyl | S | 0 | DMSO-d6: 2.10-2.30(2H, m); 3.00-3.20(2H, m); 5.00 (1H, m); 7.00-7.10(2H, m); 7.10-7.60(5H, m); 7.60-7.80 (2H, m); 13.35(1H, exchangeable, broad s) MS AP-(M-1)=355 |
| 6 | 4-trifluoromethyl-phenyl | phenyl | Se | 0 | CDCl$_3$: 2.20-2.55(2H, m); 2.90-3.30(2H, m); 4.92(1H, m); 6.80-7.00(2H, m); 7.10-7.30(3H, m); 7.40-7.60(4H, m); (N.B.: acid OH not observed) |
| 7 | 4-trifluoromethyl-phenyl | 2-methylphenyl | S | 2 | CDCl$_3$: 2.25-2.80(3H, s+ 2H, m); 3.20-3.60(2H, m); 4.88(1H, m); 6.85-7.20(3H, m); 7.20-7.45(1H, m); 7.45-7.70(3H.m); 7.80-8.15(1H, m); (N.B.: acid OH not observed). MS ES-(M-1)=401 |
| 8 | 4-trifluoromethyl-phenyl | 2-methylphenyl | S | 0 | CDCl$_3$: 2.20-2.50(3H, s+ 2H, m); 3.00-3.25(2H, m); 4.94(1H, m); 6.85-7.00(2H, |

TABLE 1-continued

| Ex. | R¹ | R² | Z | n | Characterisation data |
|---|---|---|---|---|---|
| | | | | | m); 7.00-7.20(3H, m); 7.20-7.40(1H, m)7.50-7.65(2H, m)(N.B.: acid OH not observed) |
| 9 | 4-trifluoromethyl-phenyl | 2-methylphenyl | S | 0 | CDCl₃: 2.20-2.50(3H, s+ 2H, m); 3.00-3.25(2H, m); 4.94(1H, m); 6.85-7.00(2H, m); 7.00-7.20(3H, m); 7.20-7.40(1H, m)7.50-7.65(2H, m)(N.B.: acid OH not oberved) |
| 10 | 4-tert-butylbenzyl | phenyl | S | 0 | MS AP+(M+1)=359 |
| 11 | 4-tert-butylbenzyl | 3-methoxyphenyl | S | 0 | MS AP+(M+1)=389 |
| 12 | 4-tert-butylbenzyl | 4-fluorophenyl | S | 0 | MS AP+(M+1)=377 |
| 13 | 4-tert-butylbenzyl | 8-methyl-2-phenyl-chromen-4-one | S | 0 | MS AP+(M+1)=503 |
| 14 | 4-chlorophenyl | phenyl | S | 0 | MS AP-(M-1)=321 |
| 15 | 4-chlorophenyl | 3-methoxyphenyl | S | 0 | DMSO-d6: 2.00-2.20(2H, m); 3.00-3.20(2H, m); 3.74 (3H, s); 4.85(1H, m); 6.60-6.85(1H, m); 6.85-7.10(4H, m); 7.10-7.40(3H, m); 2.06-14.00(1H, exchangeable, broad s) MS AP-(M-1)=351 |
| 16 | 4-chlorophenyl | 4-fluorophenyl | S | 0 | MS AP-(M-1)=340 |
| 17 | 4-chlorophenyl | 8-methyl-2-phenyl-chromen-4-one | S | 0 | MS AP-(M-1)=466 |
| 18 | 4-trifluoromethyl-phenyl | 3-methoxyphenyl | S | 0 | MS AP-(M-1)=385 |
| 19 | 4-trifluoromethyl-phenyl | 4-fluorophenyl | S | 0 | MS AP-(M-1)=373 |
| 20 | 4-trifluoromethyl-phenyl | 8-methyl-2-phenyl-chromen-4-one | S | 0 | DMSO-d6: 2.20-2.40(2H, m); 2.70-2.90(2H, m); 4.90-5.10(1H, m); 7.00-7.40(3H, m); 7.40-7.80(6H, m); 7.80-8.25(4H, m); 13.16(1H, exchangeable, broad s) MS AP-(M-1)=499 |
| 21 | o-cyanophenyl | 2-methylphenyl | S | 0 | MS AP-(M-1)=326 |
| 22 | 4-fluorophenyl | 3,4-dichlorophenyl | S | 0 | MS AP-(M-1)=373 |
| 23 | 4-fluorophenyl | 4-fluorophenyl | S | 0 | MS AP-(M-1)=323 |
| 24 | 4-fluorophenyl | benzothiazol-2-yl | S | 0 | MS AP-(M-1)=362 |
| 25 | o-cyanophenyl | phenyl | S | 0 | MS AP-(M-1)=312 |
| 26 | o-cyanophenyl | 3,4-dichlorophenyl | S | 0 | MS AP-(M2)=380 |
| 27 | o-cyanophenyl | 4-fluorophenyl | S | 0 | MS AP-(M-1)=330 |
| 28 | o-cyanophenyl | benzothiazol-2-yl | S | 0 | MS AP-(M-1)=369 |

TABLE 1-continued

| Ex. | R¹ | R² | Z | n | Characterisation data |
|---|---|---|---|---|---|
| 29 | 4-bromophenyl | phenyl | S | 0 | DMSO-d6: 2.00-2.20(2H, m); 3.00-3.25(2H, m); 4.58 (1H, m); 6.80-6.90(2H, m); 7.15-7.30(2H, m); 7.30-7.65 (6H, m); 13.28(1H, exchangeable, broad s) |
| 30 | 4-bromophenyl | 3,4-dichlorophenyl | S | 0 | DMSO-d6: 2.05-2.25(2H, m); 3.10-3.25(2H, m); 4.83(1H, m); 6.80-6.90 (2H, m); 7.15-7.30(1H, m); 7.30-7.50(2H, m); 7.50-7.70(2H, m); (N.B.: acid OH not observed) |
| 31 | o-phenylbenzyl | 3,4-dichlorophenyl | S | 0 | DMSO-d6: 1.80-2.00(2H, m); 2.90-3.15(2H, m); 3.90-4.00(1H, m); 4.25-4.70(2H, m); 7.20-7.30 (2H, m); 7.30-7.50(7H, m); 7.50-7.60(3H, m); 12.84(1H, exchangeable, broad s) |
| 32 | 4-{3,4-dichloro-phenyl}phenyl | 2-methylphenyl | S | 0 | CDCl₃: 2.15-2.50(3H, s+ 2H, m); 3.00-3.30(2H, m); 4.94(1H, m); 6.90-7.05(2H, m); 7.05-7.20 (3H, m); 7.20-7.40(2H, m); 7.40-7.70(4H, m) (N.B.: acid OH not observed) MS AP-(M-2)=445 |
| 33 | 4-trifluoromethyl-phenyl | 3-methylphenyl | S | 0 | MS ES-(M-1)=369 |
| 34 | 4-trifluoromethyl-phenyl | 4-methylphenyl | S | 0 | MS ES-(M-1)=369 |
| 35 | 4-trifluoromethyl-phenyl | 2,6-dimethylphenyl | S | 0 | MS ES-(M-1)=383 |
| 36 | 4-trifluoromethyl-phenyl | 2-naphthyl | S | 0 | MS ES-(M-1)=405 |
| 37 | 4-trifluoromethyl-phenyl | 1-naphthyl | S | 0 | MS ES-(M-1)=405 |
| 38 | 4-trifluoromethyl-phenyl | 2-tert-butylphenyl | S | 0 | MS ES-(M-1)=397 |
| 39 | 4-trifluoromethyl-phenyl | 2-methoxyphenyl | S | 0 | MS ES-(M-1)=385 |
| 40 | 4-trifluoromethyl-phenyl | 4-methoxyphenyl | S | 0 | MS ES-(M-1)=385 |
| 41 | 4-trifluoromethyl-phenyl | 2,4-dimethyl-phenyl | S | 0 | CDCl₃: 2.10-2.45(3H, s+ 3H, s+2H, m); 2.90-3.20 (2H, m) 4.93(1H, m); 6.80-7.05(4H, m) 7.15-7.30(1H, m); 7.45-7.60 (2H, m); (N.B.: acid OH not observed). |
| 42 | 4-trifluoromethyl-phenyl | 2,5-dimethyl-phenyl | S | 0 | CDCl₃: 2.15-2.50(3H, s+ 3H, s+2H, m); 2.95-3.20 (2H, m); 4.95(1H, m) 6.85-7.15(5H, m); 7.45-7.60(2H, m); (N.B.: acid OH not observed). |
| 43 | 4-trifluoromethyl-phenyl | 3,4-dichloro-phenyl | S | 0 | MS ES-(M-2)=423 |
| 44 | 4-trifluoromethyl-phenyl | 4-chlorophenyl | S | 0 | MS ES-(M-1)=389 |
| 45 | 4-trifluoromethyl-phenyl | 3-chlorophenyl | S | 0 | MS ES-(M-1)=389 |
| 46 | 4-trifluoromethyl-phenyl | 2-chlorophenyl | S | 0 | MS ES-(M-1)=389 |
| 47 | 4-trifluoromethyl-phenyl | 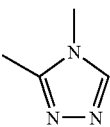 | S | 0 | MS ES-(M-1)=360 |
| 48 | 4-trifluoromethyl-phenyl | 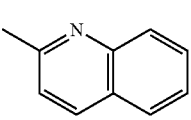 | S | 0 | MS ES+(M+1)=408 |
| 49 | 4-methoxyphenyl | 3-methylphenyl | S | 0 | MS ES-(M-1)=331 |

TABLE 1-continued

| Ex. | R¹ | R² | Z | n | Characterisation data |
|---|---|---|---|---|---|
| 50 | 4-methoxyphenyl | 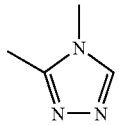 | S | 0 | MS ES−(M−1)=322 |
| 51 | 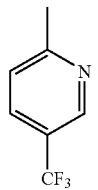 | 2-methylphenyl | S | 0 | CDCl₃: 2.20-2.45(1H, m+ 3H, s); 2.45-2.85(2H, m); 2.85-3.05(1H, m); 5.25(1H, m); 6.71(1H, m); 7.00-7.30(4H, m); 7.50-7.85(2H, m); (acid OH not observed). MS ES−(M−1)=370 |
| 52 | 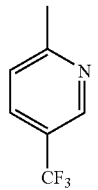 | 4-methoxyphenyl | S | 0 | MS ES−(M−1)=386 |
| 53 | 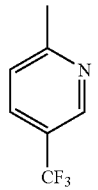 | 4-chlorophenyl | S | 0 | MS ES−(M−1)=390 |
| 54 | 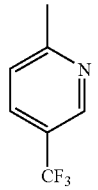 | phenyl | S | 0 | MS ES−(M−1)=356 |
| 55 | 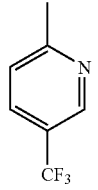 | 2-ethylphenyl | S | 0 | MS ES−(M−1)=384 |
| 56 | 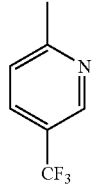 | 2,4-dimethyl-phenyl | S | 0 | CDCl₃: 2.20-2.45(3H, s+ 3H, s+1H, m); 2.45-2.75 (2H, m); 2.90-3.00(1H, m); 5.22(1H, m); 6.65-7.20(4H, m); 7.50-7.80 (2H, m); (N.B.: acid OH not observed). MS ES−(M−1)=384 |
| 57 | 4-trifluoromethyl-phenyl | CH₃ | S | 0 | CDCl₃: 2.12(3H, s); 2.25-2.45(2H, m); 2.60-2.90 (2H, m); 5.00(1H, m); 6.84(2H, d, J=8.79 Hz); 7.57(2H, d, J=8.79 Hz); (N.B.: acid OH not observed) |
| 58 | 4-trifluoromethyl-phenyl | phenyl | S | 2 | CDCl₃: 2.20-2.80(2H, m); 3.10-3.55(2H, m) 4.91(1H, m); 6.75-7.05 (2H, m); 7.40-7.80(5H, m); 7.80-8.10(2H, m); |

TABLE 1-continued

| Ex. | R¹ | R² | Z | n | Characterisation data |
|---|---|---|---|---|---|
| 59 | 4-trifluoromethyl-phenyl | 2-ethylphenyl | S | 0 | (N.B.: acid OH not observed). MS ES−(M−1)=387 CDCl₃: 1.10-1.30(3H, t, J= 7.49 Hz); 2.20-2.40 (2H, m); 2.70-2.80(2H, q, J=7.49 Hz); 3.00-3.30 (2H, m); 4.94(1H, m); 6.85-7.00(2H, m); 7.05-7.45(4H, m); 7.45-7.65 (2H, m); (N.B.: acid OH not observed). |
| 60 | 4-trifluoromethyl-phenyl |  | S | 0 | CDCl₃: 2.20-2.40(2H, m); 3.20-3.40(2H, m); 4.88(1H, m); 6.70-6.90 (2H, m); 7.35-7.50(2H, m); 7.80-8.50(4H, m); 8.85-9.00(2H, m); 9.25-9.40(1H, m)(N.B.: acid OH not observed) |

Analogously, the following compounds have been synthesized:

EXAMPLE 61

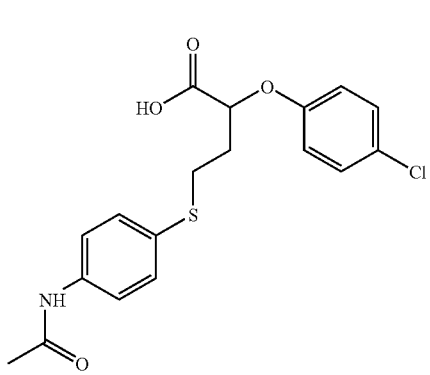

MS ES+(M+1)=380, 382.

EXAMPLE 62

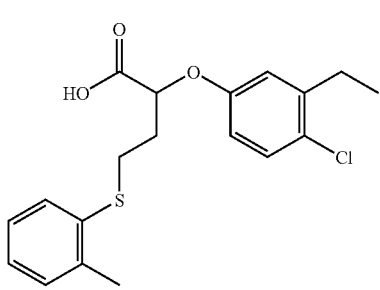

MS ES−(M−1)=363, 365.

EXAMPLE 63

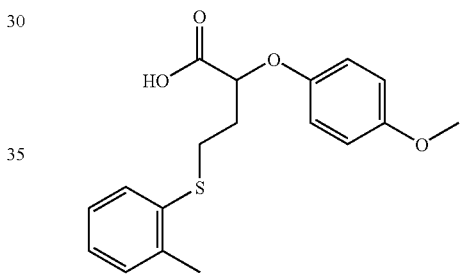

MS ES−(M−1)=331.

EXAMPLE 64

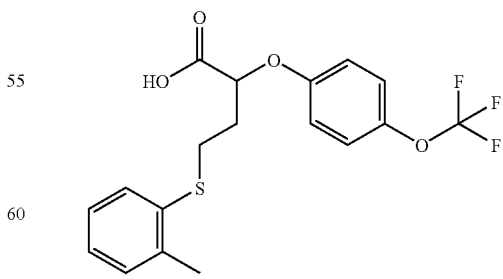

MS ES−(M−1)=385.

EXAMPLE 65
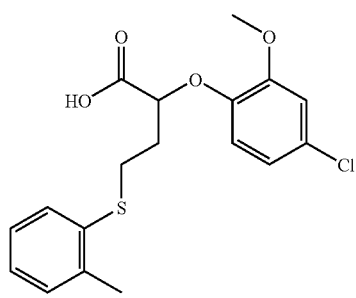
MS ES−(M−1)=365, 367.
EXAMPLE 66
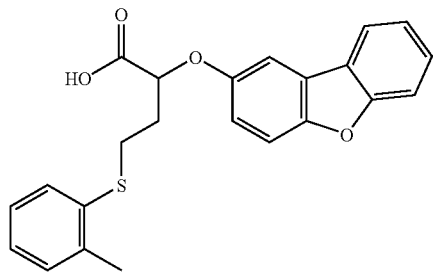
MS ES−(M−1)=391.
EXAMPLE 67
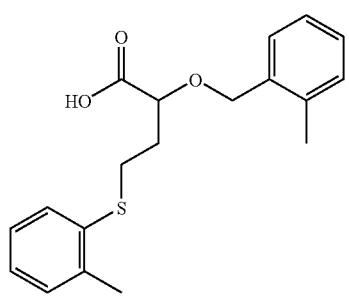
MS ES−(M−1)=329.
EXAMPLE 68
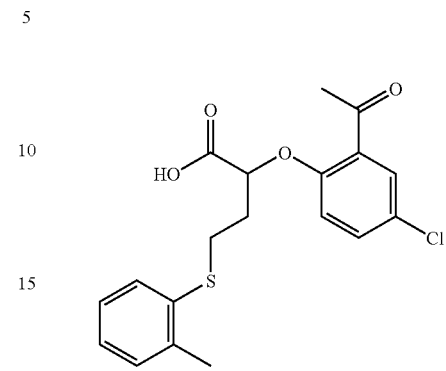
MS ES−(M−1)=377, 379.
EXAMPLE 69
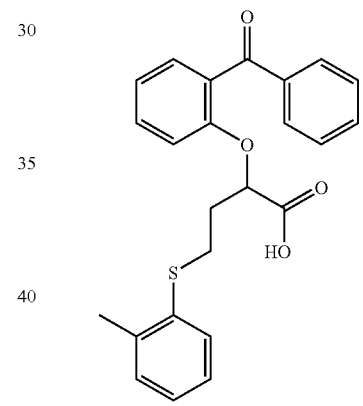
MS ES+(M+1)=407, 423.
EXAMPLE 70
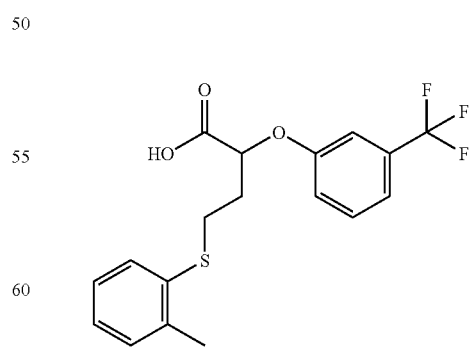
MS ES−(M−1)=369.

EXAMPLE 71
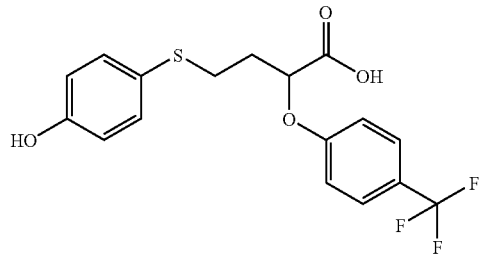
(DMSO-d6): 1.94-2.11 (2H, m); 2.80-3.03 (2H, m); 4.71-4.92 (1H, m); 6.55-6.83 (2H, m); 6.90-7.70 (2H, m); 7.12-7.33 (2H, m); 7.45-7.73 (2H, m).
NB: exchangeable protons not observed.
EXAMPLE 72
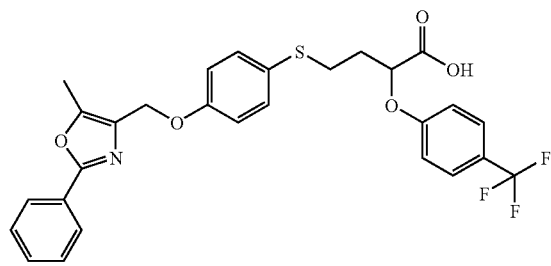
(CDCl3):1.79-2.11 (2H, m); 2.17 (3H, s); 2.59-2.93 (2H, m); 4.60-4.77 (1H, m); 4.92 (2H, s); 6.43-6.57 (2H, m); 6.62-6.76 (2H, m); 6.99-7.13 (3H, m); 7.19-7.35 (4H, m); 7.70-7.89 (2H, m).
NB: acid H not observed
EXAMPLE 73
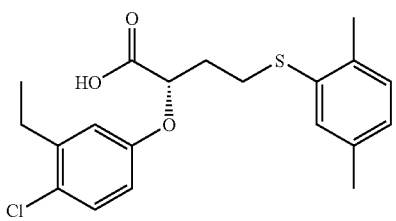
m.p. 94°C.;
(CDCl3): 1.12-1.29 (3H, m); 2.17-2.44 (8H, m); 2.60-2.81 (2H, m); 2.98-3.27 (2H, m) 4.88-5.06 (1H, m); 6.60-7.28 (6H, m); 11.24 (1H, s).
EXAMPLE 74
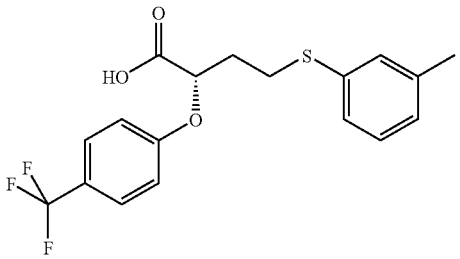
m.p. 67° C.;
(CDCl3): 02-2.57 (5H, m); 2.94-3.32 (2H, m); 4.86-5.07 (1H, m); 6.76-7.06 (3H, m); 7.06-7.30 (3H, m); 7.44-7.67 (2H, m); 9.68 (1H, broad s).
EXAMPLE 75
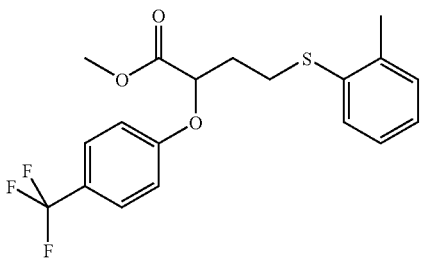
(CDCl3): 2.11-2.44 (5H, m); 2.96-3.21 (2H, m); 3.74 (3H, s); 4.80-4.97 (1H, m); 6.84-6.97 (2H, m); 7.03-7.33 (4H, m); 7.47-7.58 (2H, m).
EXAMPLE 76
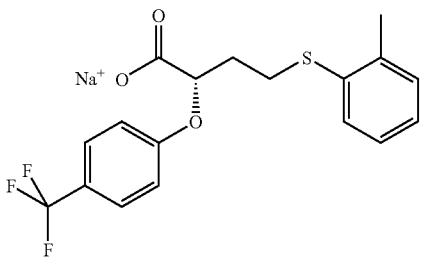
m.p. >250°C.;

(DMSO-d6): 1.95-2.18 (2H, m); 2.25 (3H, s); 2.98-3.18 (2H, m); 4.27-4.50 (1H, m); 6.83-7.22 (5H, m); 7.22-7.37 (1H, m); 7.41-7.64 (2H, m).

EXAMPLE 77

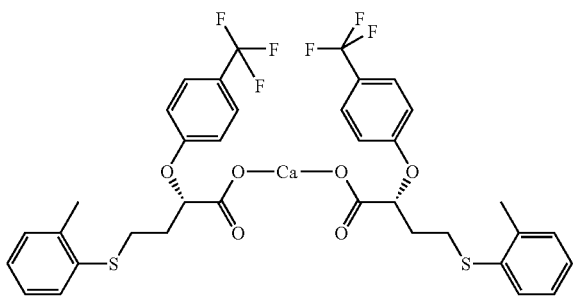

(DMSO-d6): 1.98-2.32 (10H, m); 2.96-3.17 (4H, m); 4.43-4.62 (2H, m); 6.88-7.21 (10H, m); 7.21-7.33 (2H, m); 7.44-7.58 (4H, m).

EXAMPLE 78

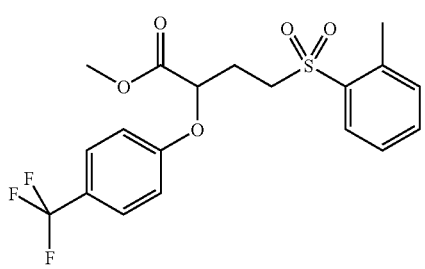

MS ES+(M+1)×417;

(CDCl3): 2.21-2.59 (2H, m); 2.67 (3H, s); 3.21-3.51 (2H, m); 3.74 (3H, s); 4.73-4.95 (1H, m); 6.72-6.95 (2H, m); 7.26-7.62 (5H, m); 7.79-8.09 (1H, m).

EXAMPLE 79

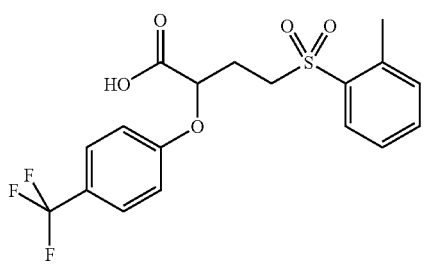

MS ES−(M−1)×401;

(CDCl3): 2.29-2.70 (5H, m); 3.22-3.54 (2H, m); 4.76-5.01 (1H, m); 6.54 (1H, broad s); 6.78-6.97 (2H, m); 7.19-7.43 (2H, m); 7.43-7.63 (3H, m); 7.87-8.08 (1H, m).

EXAMPLE 80

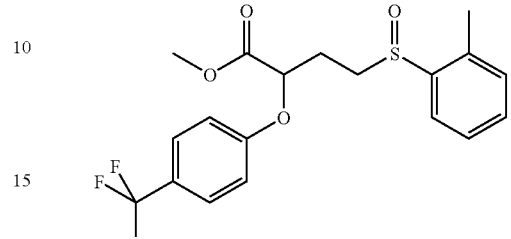

MS ES+(M+1)=401;
(CDCl3): 1.93-2.70 (5H, m); 2.70-3.22 (2H, m); 3.73 and 3.75 (3H, 2s); 4.65-4.99 (1H, m); 6.72-7.04 (2H, m); 7.07-7.63 (5H, m); 7.75-8.00 (1H, m).

EXAMPLE 81

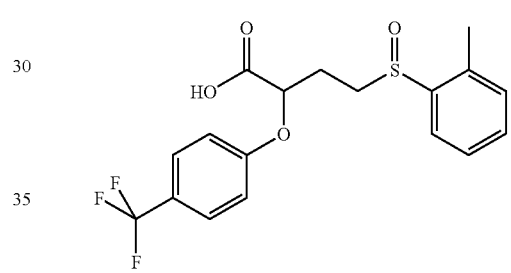

MS ES−(M−1)=385;
(CDCl3): 2.06-2.69 (5H, m); 2.87-3.32 (2H, m); 4.67-5.15 (1H, m); 5.80 (1H, broad s); 6.81-7.04 (2H, m); 7.14-7.33 (1H, m); 7.33-7.60 (4H, m); 7.79-7.99 (1H, m).

The invention claimed is:
1. Compound of the formula I:

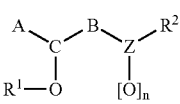

in which:
A represents carboxyl; $(C_6-C_{18})$aryloxycarbonyl in which the aryl group is optionally substituted; $(C_1-C_{14})$alkoxycarbonyl in which the alkyl group is optionally substituted; —CO—NHOH; -tetrazolyl;
B represents an optionally substituted ethylene group —CH$_2$—CH$_2$—;
$R^1$ represents a hydrogen atom; optionally substituted $(C_1-C_{14})$alkyl; optionally substituted $(C_6-C_{18})$aryl; optionally substituted heteroaryl; $(C_6-C_{18})$aryl$(C_1-C_{14})$alkyl in which each of the aryl and/or alkyl radicals are optionally substituted; and heteroaryl$(C_1-C_{14})$alkyl in which each of the heteroaryl and/or alkyl radicals are optionally substituted;

Z represents S or Se;

n is an integer equal to 0, 1 or 2;

$R^2$ represents optionally substituted ($C_6$-$C_{18}$)aryl; optionally substituted heteroaryl; or optionally substituted heterocycle containing an aromatic moiety; and when $R^1$ represents optionally substituted ($C_6$-$C_{18}$)aryl, then $R^2$ can also represent ($C_1$-$C_{14}$)alkyl; it being understood that when $R^1$ represents naphthyl or 4-methoxyphenyl, A represents carboxyl or methoxycarbonyl, B represents ethylene, n represents 0, and P represents S or Se, then $R^2$ does not represent phenyl, the stereoisomers thereof and the addition salts thereof with acids or bases.

2. Compound of the formula I according to claim 1, in which A represents —COOH.

3. Compound of the formula I according to claim 1, in which B represents ethylene.

4. Compound of the formula I according to claim 1, in which $R^1$ represents benzyl optionally substituted on the phenyl nucleus; optionally substituted phenyl; or optionally substituted pyridyl; the substituents on the phenyl nuclei and on the pyridyl nucleus preferably being chosen from halogen atoms and cyano groups, trifluoromethyl groups, ($C_1$-$C_6$) alkyl groups or ($C_1$-$C_6$)alkoxy groups or a ($C_6$-$C_{18}$)aryl group itself optionally substituted by halogen, ($C_1$-$C_6$)alkyl, ($C_1$-$C_6$)alkoxy, $CF_3$ or CN.

5. Compound of the formula I according to claim 1, in which $R^2$ represents optionally substituted phenyl; optionally substituted benzopyridine; optionally substituted benzothiazole; optionally substituted quinolyl; optionally substituted naphthyl; optionally substituted triazole; or

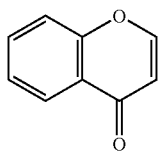

which is optionally substituted, the substituents being halogen atoms, —CN, —$CF_3$, ($C_1$-$C_6$)alkyl or ($C_1$-$C_6$)alkoxy groups or a ($C_6$-$C_{18}$)aryl group optionally substituted by halogen, ($C_1$-$C_6$)alkyl, ($C_1$-$C_6$)alkoxy, $CF_3$ or —CN.

6. Compound of the formula I according to claim 1, wherein Z represents S.

7. Process for preparing a compound of the formula I according to claim 1, in which A represents —COOH, Z represents S and n=0, comprising reacting a compound of formula II:

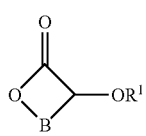

in which B and $R^1$ are as defined in claim 1, with a thiol of formula III:

in which $R^2$ is as defined in claim 1, in the presence of a base.

8. Process according to claim 7, for the preparation of an enantiomer of the formula Ib

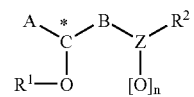

in which:

A, B, Z, $R^1$, n and $R^2$ are as defined in above and * denotes an asymmetric carbon, wherein the compound of the formula II is the enantiomer of the formula:

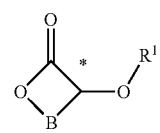

in which B and $R^1$ are as defined for formula Ib and * denotes an asymmetric carbon of the same configuration as the equivalent carbon of the formula Ib.

9. Process for preparing a compound of the formula I according to claim 1, in which A represents —COOH, Z represents Se and n=0, comprising reacting a selenium compound of formula IV:

in which $R^2$ is as defined in claim 1, with an organic or mineral base, and the resulting compound is then reacted with a compound of the formula II:

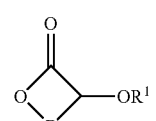

in which B and $R^1$ are as defined in claim 1 for formula I.

10. Process for preparing a compound of the formula I according to claim 1, in which A represents —COOH and n≠0, comprising reacting a compound of the formula I in which n=0:

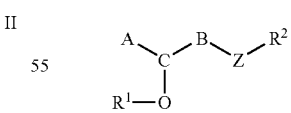

in which $R^1$, B, Z and $R^2$ are as defined in claim 1 and A represents —COOH, with an oxidizing agent.

11. Pharmaceutical composition comprising an effective amount of at least one compound chosen from a compound of the formula I according to claim 1 and the compounds of the formula I for which $R^1$ represents naphthyl or 4-methoxyphenyl; A represents carboxyl or methoxycarbonyl; B represents ethylene; n represents 0; Z represents S or Se and $R^2$ represents phenyl, in combination with at least one pharmaceutically acceptable vehicle.

12. A process according to claim 10, wherein the oxidizing is m-chloroperbensoic acid.

13. A pharmaceutical composition comprising an effective amount of a compound of claim 1 and a pharmaceutically acceptable carrier.

14. A method for treating diabetes, hyperlididemia or atherosclerosis due to hyperlipidemia, comprising administering to a host in need thereof an effective amount of a compound of claim 1.

* * * * *

UNITED STATES PATENT AND TRADEMARK OFFICE
CERTIFICATE OF CORRECTION

PATENT NO.       : 7,491,747 B2
APPLICATION NO.  : 10/485205
DATED            : February 17, 2009
INVENTOR(S)      : Didier Roche Page 1 of 1

It is certified that error appears in the above-identified patent and that said Letters Patent is hereby corrected as shown below:

On the title page, item (75), Inventors: lines 1, 2, 3, 6, and 7, reads "Lyons" should read --Lyon--

Column 40, line 11, reads "defined in above" should read --defined above--

Column 41, lines 4-5, reads "oxidizing is" should read --oxidizing agent is--

Column 41, line 5, reads "m-chloroperbensoic" should read --m-chloroperbenzoic--

Column 42, line 1, reads "hyperlididemia" should read --hyperlipidemia--

Signed and Sealed this

Twenty-ninth Day of September, 2009

David J. Kappos
*Director of the United States Patent and Trademark Office*